US011141111B2

(12) United States Patent
Fougere et al.

(10) Patent No.: US 11,141,111 B2
(45) Date of Patent: *Oct. 12, 2021

(54) VAGINAL RING SENSOR

(71) Applicant: Johnson & Johnson Consumer Inc., Skillman, NJ (US)

(72) Inventors: Richard J. Fougere, Washington Crossing, PA (US); Ming Dong, Hoboken, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 408 days.

This patent is subject to a terminal disclaimer.

(21) Appl. No.: 16/356,220

(22) Filed: Mar. 18, 2019

(65) Prior Publication Data

US 2019/0209088 A1    Jul. 11, 2019

Related U.S. Application Data

(63) Continuation of application No. 15/263,618, filed on Sep. 13, 2016, now Pat. No. 10,314,540.
(Continued)

(51) Int. Cl.
*A61B 5/00* (2006.01)
*A61B 5/145* (2006.01)
(Continued)

(52) U.S. Cl.
CPC .......... *A61B 5/6847* (2013.01); *A61B 5/0002* (2013.01); *A61B 5/01* (2013.01); *A61B 5/024* (2013.01); *A61B 5/0215* (2013.01); *A61B 5/07* (2013.01); *A61B 5/1459* (2013.01); *A61B 5/1473* (2013.01); *A61B 5/14507* (2013.01); *A61B 5/14539* (2013.01); *A61B 5/14546* (2013.01); *A61B 5/4337* (2013.01);
(Continued)

(58) Field of Classification Search
CPC .............. A61B 5/6847; A61B 5/14546; A61B 5/14507; A61B 5/0002; A61B 5/14539; A61B 5/0215; A61B 5/1473; A61B 5/4337; A61B 5/01; A61B 5/024; A61B 5/4875; A61B 5/1459; A61B 5/021; A61B 5/0084; A61B 5/165; A61B 5/1486; A61B 5/14865; A61B 5/14532; A61B 5/0011; A61B 5/14503
See application file for complete search history.

(56) References Cited

U.S. PATENT DOCUMENTS 5,406,961 A * 4/1995 Artal .................... A61B 5/1076
600/587
6,363,271 B1    3/2002 Berry
(Continued)

FOREIGN PATENT DOCUMENTS

RU            157446 U1    12/2015

OTHER PUBLICATIONS

PCT International Search Report dated Jan. 18, 2017 for corresponding International Application No. PCT/US2016/051444.

*Primary Examiner* — Chu Chuan Liu

(57) ABSTRACT

A vaginal ring sensor device adapted to be placed within the vaginal vault of a user, the device including a ring body, at least one through hole that passes through the ring body, and at least one biosensor structured and arranged to sense and/or measure a parameter of vaginal fluid as such fluid passes through the at least one through hole.

29 Claims, 4 Drawing Sheets

Related U.S. Application Data

(60) Provisional application No. 62/221,786, filed on Sep. 22, 2015.

(51) Int. Cl.

| | | |
|---|---|---|
| *A61B 5/01* | (2006.01) | |
| *A61B 5/0215* | (2006.01) | |
| *A61B 5/024* | (2006.01) | |
| *A61B 5/1473* | (2006.01) | |
| *A61B 5/1459* | (2006.01) | |
| *A61M 31/00* | (2006.01) | |
| *A61B 5/07* | (2006.01) | |
| *A61B 5/021* | (2006.01) | |
| *A61B 5/1486* | (2006.01) | |
| *A61B 5/16* | (2006.01) | |

(52) U.S. Cl.
CPC ........... *A61B 5/4875* (2013.01); *A61M 31/00* (2013.01); *A61B 5/0011* (2013.01); *A61B 5/0071* (2013.01); *A61B 5/0084* (2013.01); *A61B 5/021* (2013.01); *A61B 5/1486* (2013.01); *A61B 5/14503* (2013.01); *A61B 5/14532* (2013.01); *A61B 5/14865* (2013.01); *A61B 5/165* (2013.01); *A61B 5/4318* (2013.01); *A61B 5/746* (2013.01); *A61B 2562/12* (2013.01); *A61M 2210/1475* (2013.01)

(56) References Cited

U.S. PATENT DOCUMENTS

| | | | |
|---|---|---|---|
| 6,514,214 B2* | 2/2003 | Kokate | A61B 5/01 |
| | | | 600/505 |
| 2002/0111560 A1 | 8/2002 | Kokate et al. | |
| 2006/0084848 A1 | 4/2006 | Mitchnick | |
| 2011/0190579 A1 | 8/2011 | Ziarno | |
| 2012/0016258 A1* | 1/2012 | Webster | A61B 5/01 |
| | | | 600/549 |
| 2013/0237771 A1 | 9/2013 | Runkewitz | |
| 2014/0243922 A1 | 8/2014 | Haessler | |

* cited by examiner

VAGINAL RING SENSOR

CROSS REFERENCE TO RELATED APPLICATIONS

This application is a continuation of U.S. application Ser. No. 15/263,618 filed Sep. 13, 2016 (pending) which claims the benefit of U.S. Provisional Patent Application Ser. No. 62/221,786 filed on Sep. 22, 2015.

FIELD OF THE INVENTION

The present invention relates to a device for real-time biometric sensing and real-time biomarker sensing via a wet interface within the body without tissue trauma. More particularly, the present invention relates to a ring shaped device for sensing biomarkers via a wet interface within in the vaginal vault of a female.

BACKGROUND OF THE INVENTION

Advances in microelectronics, material science and wireless technology have led to the development of sensors that can be used for accurate monitoring of previously inaccessible environments. Health monitoring, telemedicine, military and environmental monitoring are some of the applications where sensors can be used. Sensors used in connection with health monitoring may be applied to the external surface of the body or implanted inside the human body. Such sensors are referred to herein as "biosensors." Biosensors may be used individually to monitor a particular part of the body or multiple sensors can be used in combination to form a network and collectively monitor the health condition of their carrier or host. Biosensors are often implanted inside the human body because biomarker sensing via a wet interface within the body may be required depending upon the particular biomarker being sensed and/or measured. Implantation typically requires a surgical procedure with the accompanying risks associated with surgery.

Vaginal rings, i.e. ring shaped devices intended to be inserted into the vaginal vault are also well known in the art. Vaginal rings of the type taught in the prior art are typically used either as drug delivery systems or as core body temperature monitors. In general, these devices are ring shaped, and comprise a pharmaceutically acceptable inert material. In some embodiments, the vaginal rings are elastic so as to be easily inserted into the vaginal vault of the user without a surgical procedure.

Some prior art vaginal rings intended for use as drug delivery systems have been constructed to include blind holes and through holes which are filled with the drug to be delivered to the vaginal region. The filled holes do not allow for flow of vaginal fluids through the body of the ring.

In summary, although known biosensors may be used to monitor the health condition of their carrier or host they typically require invasive surgical implantation if the monitoring of a wet interface is desired. Accordingly it is an objective of the present invention to provide a biosensor that can readily be placed within the body, in a location with a wet interface, without the need for surgical implantation.

SUMMARY OF THE INVENTION

The present invention provides, according to a first aspect of the invention, a vaginal ring sensor device including a ring body, at least one through hole that passes through the ring body, and at least one biosensor structured and arranged to sense and/or measure a parameter of vaginal fluid as such fluid passes through said at least one through hole.

The present invention provides, according to a second aspect of the invention, a vaginal ring sensor device including a ring body, a plurality of through holes that pass through the ring body, and at least one biosensor structured and arranged to sense and/or measure a parameter of vaginal fluid as such fluid passes through at least one of the through holes.

The present invention provides, according to a third aspect of the invention, a method of using a vaginal ring sensor device including the steps of inserting a vaginal ring sensor device having at least one through hole the passes through a ring body of the vaginal ring sensor device into the vaginal vault of a user, and measuring and/or sensing at least one parameter of a vaginal fluid that passes through the at least one through hole.

DETAILED DESCRIPTION OF THE INVENTION

Biosensors inserted within the human body can be used to sense biomarker information via a wet interface within the body. One area inside the body with wet interfaces is within the vaginal vault. There are many fluids within the vaginal vault that can be used for wet interface sensing. Some of these fluids include vaginal transudate, Bartholin's and Skene's glands secretions, cervical mucus, exfoliated epithelial cells, and fluid from the uterus and endometrial tubes. The vaginal ring sensor device of the present invention is adapted to sense biomarker information via the wet interface located within the vaginal vault.

Figure 1:
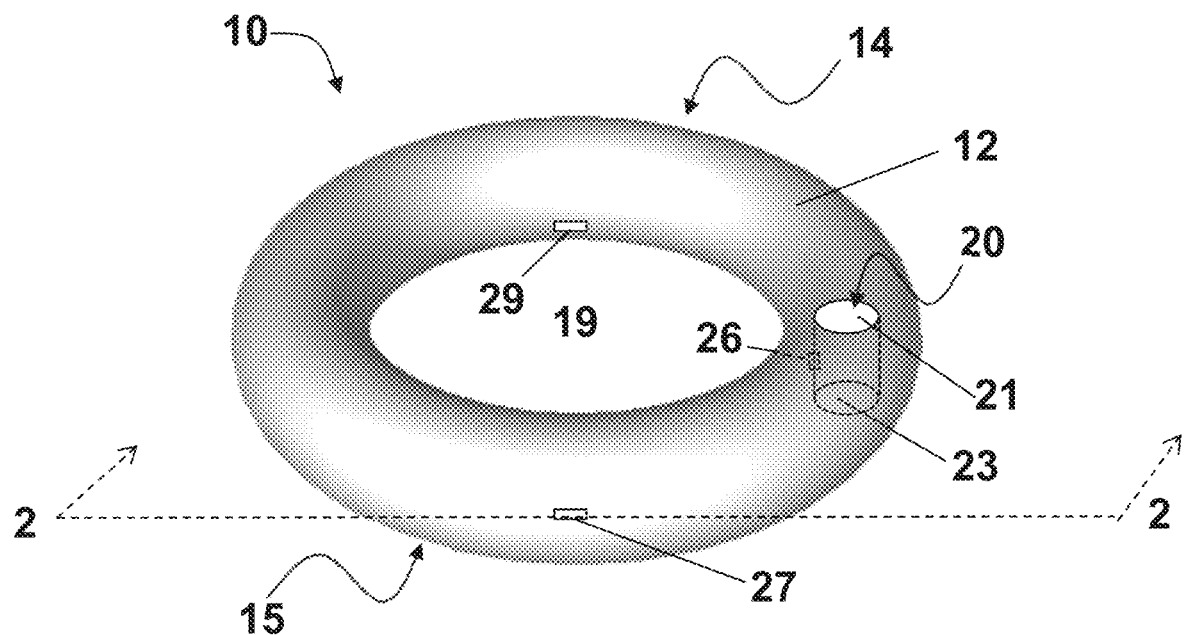
FIG. 1 is a perspective view of a vaginal ring sensor device according a first embodiment of the present invention.
Figure 2:
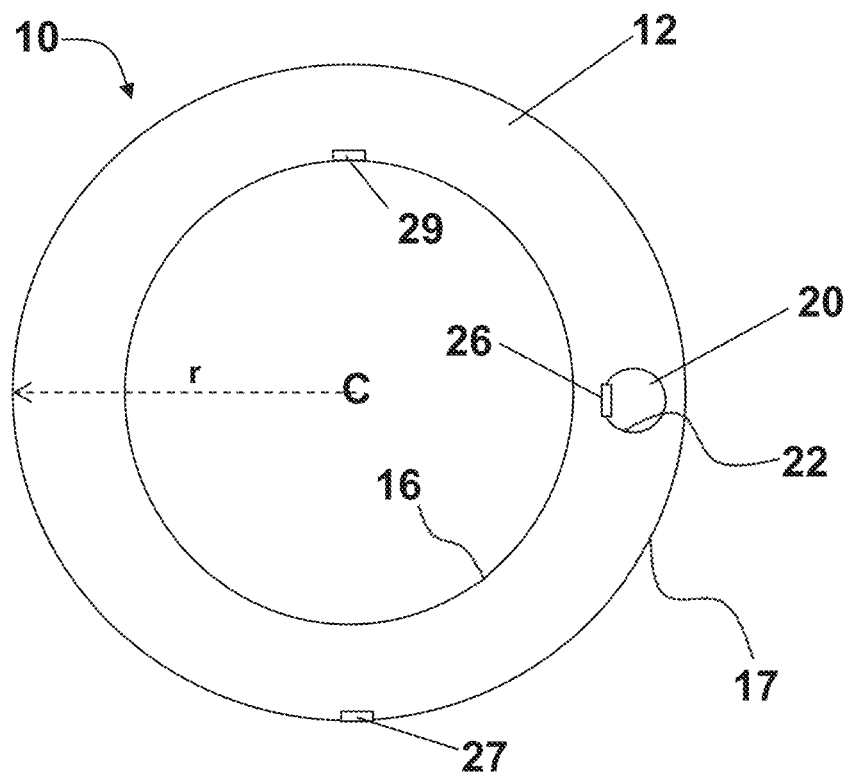
FIG. 2 is a cross-sectional view taken along line 2-2 of the vaginal ring sensor device of FIG. 1.

A first embodiment of a vaginal ring sensor device 10 according to the present invention is shown in FIGS. 1 and 2. The vaginal ring sensor device 10 includes a ring body 12 having a first surface 14 and a second surface 15. Second surface 15 is opposite first surface 14, and first surface 14 and second surface 15 may also be referred to as top 14 and bottom 15 surfaces, respectively. The vaginal ring sensor device 10 further includes at least one through hole 20 that passes through the ring body 12. In the embodiment of the invention shown in FIGS. 1 and 2 the through hole 20 extends from the first surface 14 to the second surface 15. The through hole 20 includes a first opening 21 and a opposed second opening 23. The through hole 20 functions to define a through surface 22 extending through the ring body 12 from the first opening 21 to the second opening 23. As shown in FIG. 2, in addition to having top 14 and bottom 15 surfaces, the ring body 12 also has an inner surface 16 and an outer surface 17. The ring 12 is preferably sized so that it can be easily inserted into the vaginal vault of a female user, be securely retained within the vaginal vault during use, and easily removed by the user. For a human female, the ring 12 may have, for example, a radius of 2 to 3 centimeters, wherein the radius "r" is measured from the center "C" of the hole 19 defined by the ring body 12 to the outer surface 17 of ring body 12. The specific radius of ring 12 may be selected to suit the particular anatomy of the user to maximize comfort for the individual.

Through hole 20 is structured and arranged to allow the fluids within the vaginal area to flow through the ring body 12 immediately upon insertion of the device 10 into the vaginal vault and throughout the time that the user maintains the device 10 within the vaginal vault. As will be discussed in greater detail below, this structure allows for wet interface sensing of the fluids in the vaginal area.

FIGS. 1 and 2 show vaginal ring sensor device 10 as having a ring body 12 in the shape of a torus, that is a loop of material having a round, or circular, cross-section. Though shown as a torus, the ring body 12 may be structured to have other shapes and other cross-sectional profiles. For example, the ring body 12 may be structured to have an oval, square, triangular, square, race track, or other suitable shape. Also the ring body 12 may be structured to have a cross-sectional shape that is oval, race track, triangular, square, x-shaped, rectangular, rounded rectangle, or other suitable shape. The ring body 12 is preferably sized so that its cross section, measures in the range from about 7 mm to about 10 mm. However these dimensions may be varied depending upon the particular material characteristics of the material used to form the ring body 12 and the anatomy and comfort considerations of the individual user.

FIGS. 1 and 2 show vaginal ring sensor device 10 having at least one through 20. Other embodiments of vaginal ring sensor device 10 of the present invention may have a plurality of through holes 20, for example at least two, three, four, six, twelve, sixteen, twenty-four, or any number of through holes 20 as desired for the particular application of the invention.

FIGS. 1 and 2 depict the through hole 20 as having a round, or circular shape. However the through hole 20 may be structured and arranged to have other shapes. For example, the through hole 20 may be structured to be oval, race track, triangular, square, rectangular, rounded rectangle, or any other suitable shape that readily permits fluid to pass through the ring body 12 immediately upon insertion of the device 10 into the vaginal vault and throughout the time that the user maintains the device 10 within the vaginal vault. In embodiments with multiple through holes 20, the through holes 20 may have a variety of shapes, for example a combination of round and square through holes 20. In still other embodiments, some or all through holes 20 may be tapered as they pass from first surface 14 to second surface 15 of ring body 12 or vice versa.

As shown in FIG. 2, the vaginal ring sensor device 10 according to the present invention further includes at least one biosensor 26. The biosensor 26 is structured and arranged such that it can sense and/or measure a parameter of a fluid as such fluid passes through a through hole 20. Preferably the biosensor 26 is arranged on the through surface 22 of the ring body 12 between the first opening 21 and second opening 23. In the particular embodiment of the invention depicted in FIG. 2 a single biosensor 26 is arranged on the through surface 22 of the ring body 12. However, other embodiments of the present invention may include two or more biosensors 26 arranged on the through surface 22 of the ring body 12. In some embodiments of the present invention including multiple through holes 20 the ring sensor device 10 may include one, two or more biosensors 26 arranged in a single through hole 20, while other through holes 20 have no biosensors 26.

In the embodiment shown in FIG. 2, biosensor 26 is shown as partially embedded into the through surface 22 of the ring body 12. In this way, the material comprising ring body 12 will hold biosensor 26 in place. In other embodiments, biosensor 26 may be secured to the through surface 22. For example, adhesives may be used to keep the biosensor in place. In embodiments where biosensor 26 is embedded into the through surface 22 of the ring body 12, the biosensors may be embedded during the processing of the vaginal ring sensor device 10 using techniques such as insert molding. In still other embodiments, some biosensors 26 may be partially embedded into the through surface 22 within some of the through holes 20, while other are secured to the through surface 22 of some of the through holes 20.

As shown in FIG. 2, the vaginal ring sensor device 10 may optionally further include at least one biosensor 27 arranged on an outer surface 17 of the ring body 12. In the particular embodiment of the invention depicted in FIG. 2 a single biosensor 27 is arranged on the outer surface 17 of the ring body 12. However, other embodiments of the present invention may include two or more biosensors 27 arranged on the outer surface 17 of the ring body 12. In the embodiment shown in FIG. 2, biosensor 27 is shown as partially embedded into the outer surface 17 of the ring body 12. In this way, the material comprising ring body 12 will hold biosensor 27 in place. In other embodiments, biosensor 27 may be secured to the outer surface 17. For example, adhesives may be used to keep the biosensor 27 in place. In embodiments where biosensor 27 is partially embedded into the outer surface 17 of the ring body 12, the biosensor may be embedded during the processing of the ring body 12 using techniques such as insert molding.

As shown in FIG. 2, the vaginal ring sensor device 10 may optionally further include at least one biosensor 29 arranged on an inner surface 16 of the ring body 12. In the particular embodiment of the invention depicted in FIG. 2 a single biosensor 29 is arranged on the inner surface 16 of the ring body 12. However, other embodiments of the present invention may include two or more biosensors 29 arranged on the inner surface 16 of the ring body 12. In the embodiment shown in FIG. 2, biosensor 29 is shown as partially embedded into the inner surface 16 of the ring body 12. In this way, the material comprising ring body 12 will hold biosensor 29 in place. In other embodiments, biosensor 29 may be secured to the inner surface 16. For example, adhesives may be used to keep the biosensor 29 in place. In embodiments where biosensor 29 is partially embedded into the inner surface 16 of the ring body 12, the biosensor may be embedded during the processing of the ring body 12 using techniques such as insert molding.

Figure 3:
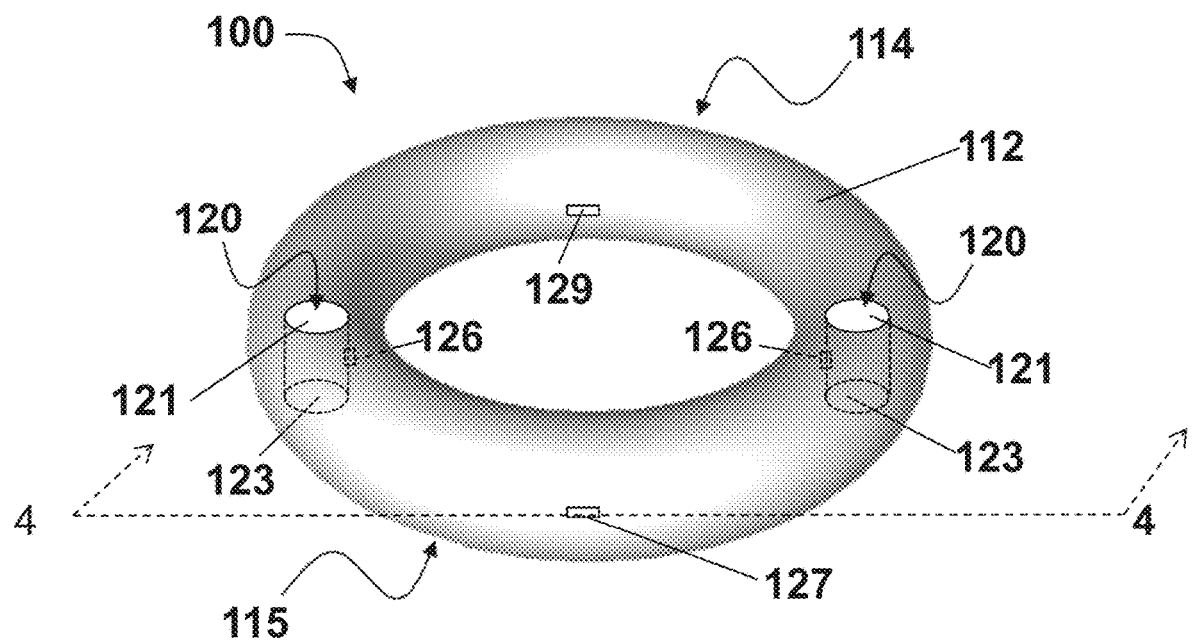
FIG. 3 is a perspective view of a vaginal ring sensor device according to a second embodiment of the present invention.
Figure 4:
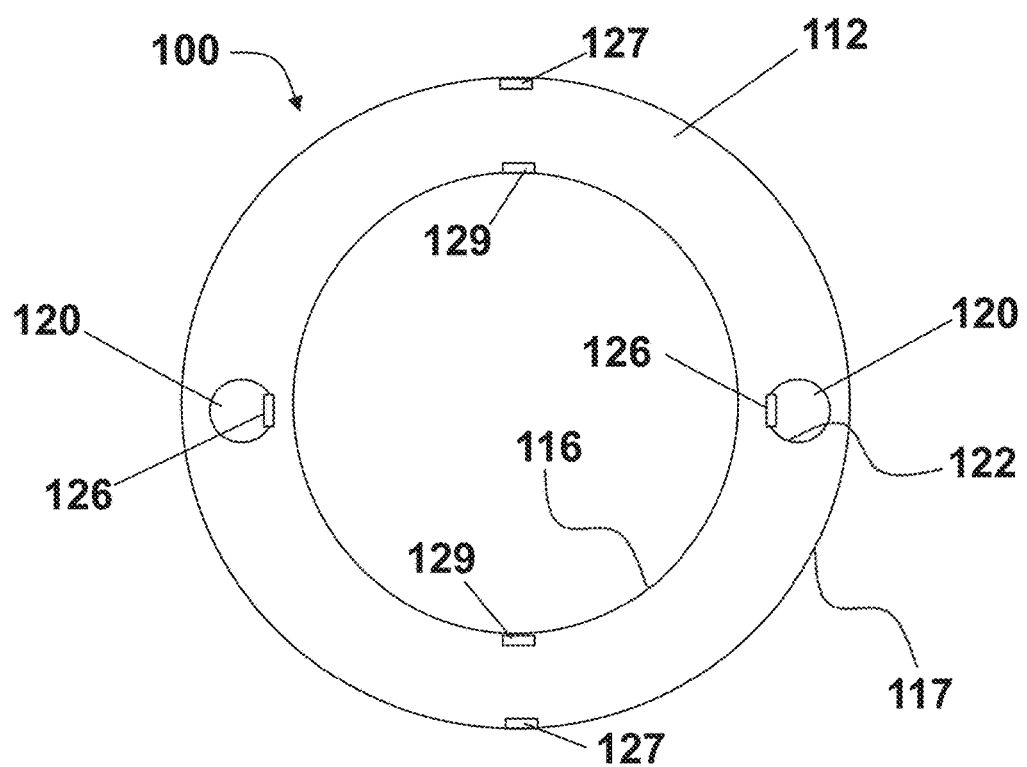
FIG. 4 is a cross-sectional view taken along line 4-4 of the vaginal ring sensor device of FIG. 3.

A second embodiment of a vaginal ring sensor device 100 according to the present invention is shown in FIGS. 3 and 4. FIGS. 3 and 4 show a vaginal ring sensor device 100 having a plurality of through holes 120, and more particularly in the specific embodiment depicted, two through holes 120. Other embodiments of vaginal ring sensor device 100 of the present invention may include any suitable number of through holes 120, for example at least three, four, six, twelve, sixteen, twenty-four, or any number of through holes 120 as desired for the particular application of the invention.

FIGS. 3 and 4 depict each of the through holes 120 as having a round, or circular shape. However the through holes 120 may be structured and arranged to have other shapes. For example, the through holes 120 may be structured to be oval, race track, triangular, square, rectangular, rounded rectangle, or any other suitable shape that readily permits fluid to pass through the ring body 112 immediately upon insertion of the device 100 into the vaginal vault and throughout the time that the user maintains the device 100 within the vaginal vault. In embodiments with multiple through holes 120, the through holes 120 may have a variety of shapes, for example a combination of round and square through holes 120. In still other embodiments, some or all through holes 120 may be tapered as they pass from first surface 114 to second surface 115 of ring body 112 or vice versa.

As shown in FIG. 4, the vaginal ring sensor device 100 according to the present invention further includes at least one biosensor 126. The biosensor 126 is structured and arranged such that it can sense and/or measure of a parameter of a fluid as such fluid passes through a through hole 120. Preferably the biosensor 126 is arranged on the through surface 122 of the ring body 112 between the first opening 121 and second opening 123. In the particular embodiment of the invention depicted in FIG. 4 a single biosensor 126 is arranged on the through surface 122 of the ring body 112. However, other embodiments of the present invention may include two or more biosensors 126 arranged on the through surface 122 of the ring body 112. In some embodiments of the present invention including multiple through holes 120 the ring sensor device 100 may include one, two or more biosensors 126 arranged in a single through hole 120, while other through holes 120 have no biosensors 126.

In the embodiment shown in FIG. 4, biosensors 126 are shown as partially embedded into the through surface 122 of the ring body 112. In this way, the material comprising ring body 112 will hold biosensor 126 in place. In other embodiments, biosensors 126 may be secured to the through surface 122. For example, adhesives may be used to keep the biosensors 126 in place. In embodiments where biosensors 126 are embedded into the through surface 122 of the ring body 112, the biosensors may be embedded during the processing of the vaginal ring sensor device 110 using techniques such as insert molding. In still other embodiments, some biosensors 126 may be partially embedded into the through surface 122 within some of the through holes 120, while other are secured to the through surface 122 of some of the through holes 120.

As shown in FIG. 4, the vaginal ring sensor device 100 may optionally further include at least one biosensor 127 arranged on an outer surface 117 of the ring body 120. In the particular embodiment of the invention depicted in FIG. 4 two biosensors 127 are arranged on the outer surface 117 of the ring body 112. However, other embodiments of the present invention may include a single biosensor, or three or more biosensors 127 arranged on the outer surface 117 of the ring body 112. In the embodiment shown in FIG. 4, biosensors 127 are shown as partially embedded into the outer surface 117 of the ring body 112. In this way, the material comprising ring body 112 will hold the biosensor 127 in place. In other embodiments, biosensors 127 may be secured to the outer surface 117. For example, adhesives may be used to keep the biosensors 127 in place. In embodiments where biosensors 127 are partially embedded into the outer surface 117 of the ring body 112, the biosensors may be embedded during the processing of the ring body 112 using techniques such as insert molding.

As shown in FIG. 4, the vaginal ring sensor device 100 may optionally further include at least one biosensor 129 arranged on an inner surface 116 of the ring body 112. In the particular embodiment of the invention depicted in FIG. 4 two biosensors 129 are arranged on the inner surface 116 of the ring body 112. However, other embodiments of the present invention may include a single biosensor, or three or more biosensors 129 arranged on the inner surface 116 of the ring body 112. In the embodiment shown in FIG. 4, biosensors 129 are shown as partially embedded into the inner surface 116 of the ring body 112. In this way, the material comprising ring body 112 will hold the biosensor 129 in place. In other embodiments, biosensors 129 may be secured to the inner surface 116. For example, adhesives may be used to keep the biosensors 129 in place. In embodiments where biosensors 129 are partially embedded into the inner surface 116 of the ring body 112, the biosensors may be embedded during the processing of the ring body 112 using techniques such as insert molding.

Figure 5:
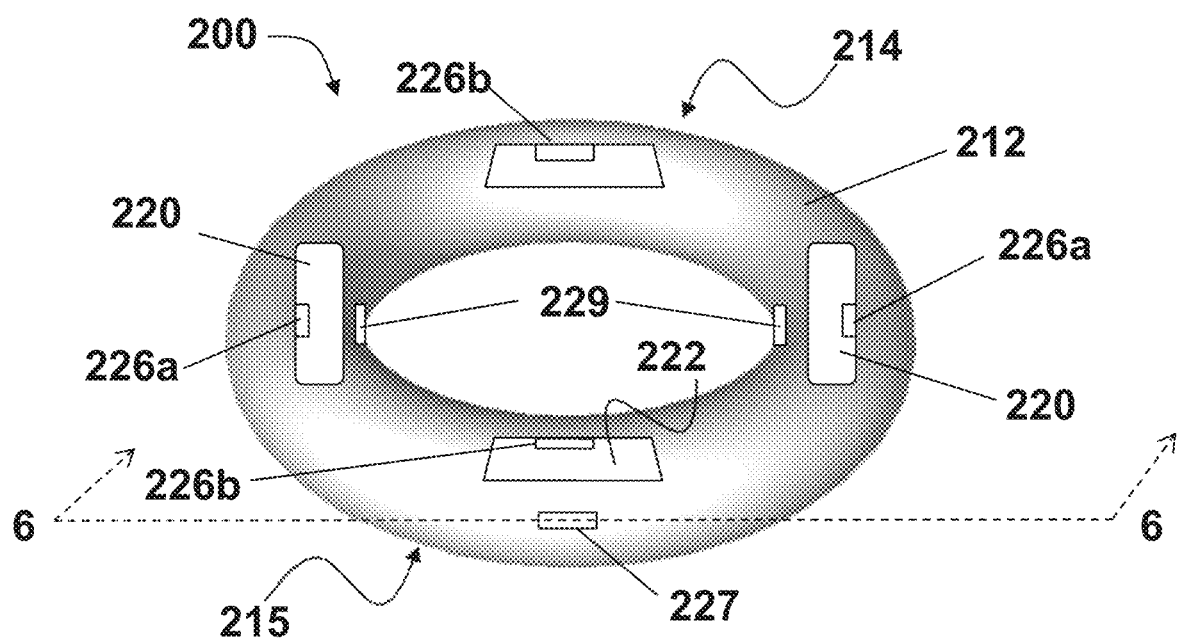
FIG. 5 is a perspective view of a vaginal ring sensor device according to a third embodiment of the present invention.
Figure 6:
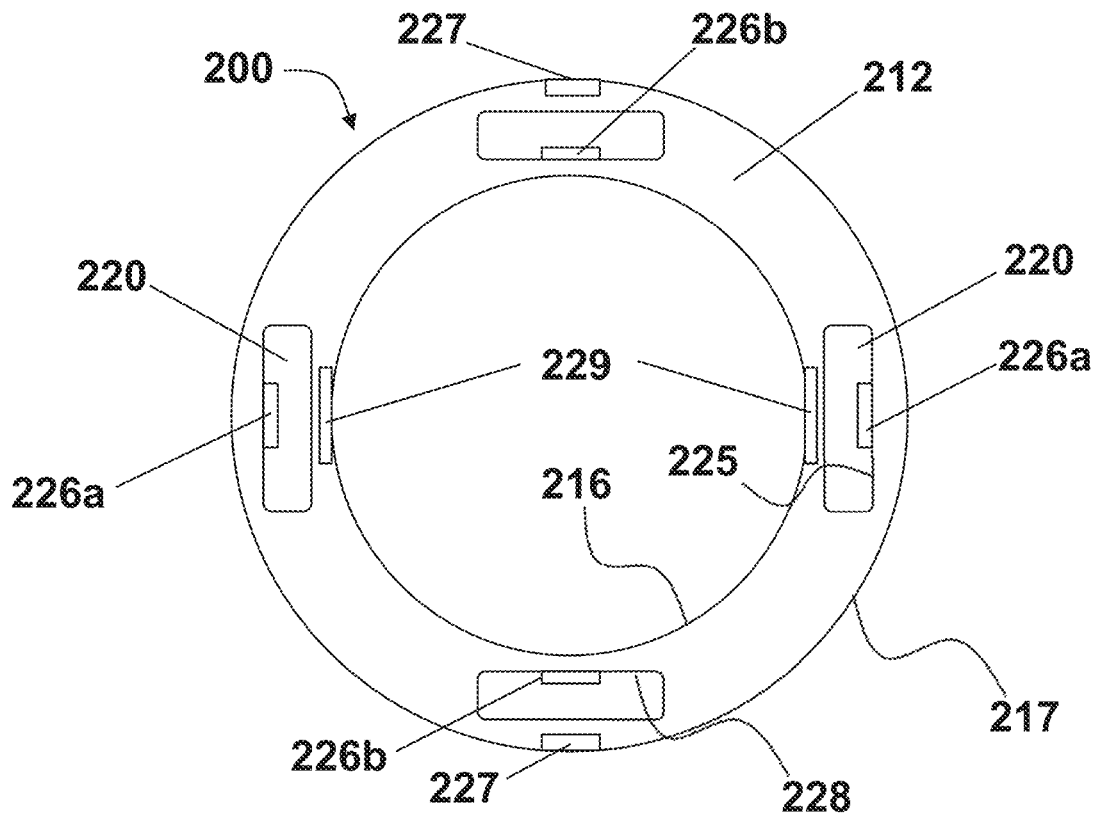
FIG. 6 is a cross-sectional view taken along line 6-6 of the vaginal ring sensor device of FIG. 5.

A third embodiment of a vaginal ring sensor device 200 according to the present invention is shown in FIGS. 5 and 6. FIGS. 5 and 6 show a vaginal ring sensor device 200 having a plurality of through holes 220, and more particularly in the specific embodiment depicted four through holes 220. Other embodiments of vaginal ring sensor device 200 of the present invention may include any suitable number of through holes 220, for example six, twelve, sixteen, twenty-four, or any number of through holes 220 as desired for the particular application of the invention.

FIGS. 5 and 6 depict each of the through holes 220 as having a rounded rectangular shape. However the through holes 220 may be structured and arranged to have other shapes. For example, the through holes 220 may be structured to be oval, race track, square, rectangular, or any other suitable shape that readily permits fluid to pass through the ring body 212 immediately upon insertion of the device 200 into the vaginal vault and throughout the time that the user maintains the device 200 within the vaginal vault. In embodiments with multiple through holes 220, the through holes 220 may have a variety of shapes, for example a combination of round and square through holes 220. In still other embodiments, some or all through holes 220 may be tapered as they pass from first surface 214 to second surface 215 of ring body 212 or vice versa.

As shown in FIG. 6, the vaginal ring sensor device 200 according to the present invention further includes a first pair of biosensors 226a. Each one of the biosensors 226a is structured and arranged such that it can sense and/or measure a parameter of a fluid as such fluid passes through a through hole 220. Each biosensor 226a is arranged within a respective through hole 220, and specifically on an outer wall 225 of the through surface 222. In the particular embodiment shown in FIG. 6, each of the biosensors 226a are arranged such that they are directionally aligned with one another, that is they are located within through holes 220 that are directional aligned with one another on opposite sides of the ring body 212.

The vaginal ring sensor device 200 further includes a second pair of biosensors 226b. Each biosensor 226b is arranged within a respective through hole 220, and specifically on an inner wall 228 of the through surface 222. In the particular embodiment shown in FIG. 6, each of the biosensors 226b are arranged such that they are directionally aligned with one another, that is they are located within through holes 220 that are directional aligned with one another on opposite sides of the ring body 212.

As shown in FIG. 6, the vaginal ring sensor device 200 may optionally further include at least one biosensor 227 arranged on an outer surface 217 of the ring body 212. In the particular embodiment of the invention depicted in FIG. 6 two biosensors 227 are arranged on the outer surface 217 of the ring body 212. In the particular embodiment of the invention shown FIG. 6, each one of the biosensors 227 are directionally aligned with one another, that is they are directionally aligned on opposite sides of the ring body 212.

As shown in FIG. 4, the vaginal ring sensor device 200 may optionally further include at least one biosensor 229 arranged on an inner surface 216 of the ring body 212. In the particular embodiment of the invention depicted in FIG. 6 two biosensors 229 are arranged on the inner surface 216 of the ring body 212. In the particular embodiment of the invention shown FIG. 6, each one of the biosensors 229 are directionally aligned with one another, that is they are directionally aligned on opposite sides of the ring body 212.

The vaginal ring body 12, 112, or 212 of the invention may be comprised of numerous pharmaceutically acceptable inert materials. Particular examples of such a pharmaceutically acceptable inert material include poly(ethylene-co-vinyl acetate) (PEVA), polyethylene (PE), polypropylene (PP), polyvinyl chloride (PVC), polyamide-imide (PAI), polyamide (PA), cross-linked polyethylene (PEX), thermoplastic elastomers (TPE), thermoplastic polyurethanes (TPUs), thermoplastic vulcanizates (TPVs), polybutylene terephthalate (PBT), polyester, poly(ethylene terephthalate) (PET), silicone elastomers, cellulose derivatives, thermoplastic rubber, and polydimethylsiloxane, and copolymers and blends made with one or more of the above materials to name only a few.

The vaginal ring sensor device 10, 100, or 200 of the invention includes electronics for sensing and/or measuring physiological parameters in the vaginal vault of a female user. "Electronics" generally refers to a device incorporating a plurality of components, and includes large area electronics, printed wire boards, integrated circuits, component arrays, biological and/or chemical biosensors, and physical biosensors. The electronics may also comprise transmission components. The sensing and transmission arrangement may be comprised by a flexible circuit board arrangement. The flexible circuit board arrangement is size adapted to be accommodated by or within the ring body 12, 112, or 212. The flexible circuit board arrangement can be a sensing element and a transmission element which is a miniature electronic circuit that generally can comprise for example an antenna, a radio transmitter, a small silicon-based microcontroller with memory, and a single, or series of biosensors.

Vaginal ring sensor device 10, 100, or 200 can be an active radio frequency device consistent with embodiments of the present invention. The flexible circuit board arrangement can support an active transmitter element. The active transmitter element generally can comprise one or more biosensors; conditioning circuitry that can include a number of discrete components, such as capacitors, resistors, and diodes; a small silicon-based microcontroller that interfaces with the one or more biosensors; solid state memory; a radio transmitter; battery and voltage regulation circuits; and an antenna. The radio transmitter can interface with the user, or with a health care professional via a computer, tablet, or smart phone.

The radio transmitter, of radio frequency (RF) device, can be a type of electronic data generating and memory device which can provide a means for measuring and providing information about the biosensor input. The vaginal ring sensor device 10, 100, or 200 can be considered an active device when, in certain embodiments, it possesses its own discrete power source, such as a battery. Such an active device can be programmed to periodically transmit recently measured physiological measurements, periodically transmit several stored physiological readings or it can emit a signal containing its stored information whenever it enters and is queried by an RF field. In other embodiments, the radio transmitter assembly can be a passive radio frequency (RF) device. Unlike the active device described above, passive radio frequency transponder devices do not contain a power source. Rather, they generally operate in an RFID environment and are inductively or capacitively powered when they enter an RF field. Once powered, the passive and/or optionally semi-passive (battery assisted) transponder Integrated Circuit (IC) can measure physiological property and emit a signal containing this measured information. Both active and passive radio frequency devices can include an analog circuit that detects and decodes data contained in the interrogating RF signal providing data to the active or passive radio frequency. The microcontroller circuit in the active device and digital circuitry contained in the transponder IC in the passive device generally executes the data functions of the radio frequency sensor and transmission device, such as measuring temperature, digitizing the data and causing the digital data to modulate the RF signal to transmit the measured data. In addition to retrieving and transmitting real-time measured data, both passive and active devices can permit new or additional information to be written to a portion of the radio frequency device's memory, and/or, optionally, can permit the device to manipulate data or perform some additional functions.

"Sensing" refers to detecting the presence, absence, amount, magnitude or intensity of a physical and/or chemical property. Useful electronic device components for sensing include, but are not limited to electrode elements, chemical or biological sensor elements, pH sensors, temperature sensors and capacitive sensors.

Biosensors 26, 27, 29, 126, 127, 129, 226*a*, 226*b*, 227, 229 may be used for sensing and/or measuring physiological parameters in the vaginal vault of a female user. Physical parameters may include, but are not limited to: blood pressure, heart rate, pulse wave, pulse oximeter, temperature, or hydration.

The vaginal ring sensor device 10, 100, 200 of the invention may include a data storage device for recording the measured and/or sensed physiological parameters until such time as the device is removed. At such time the measured data may be transferred to from the ring sensor device to a CPU or other tool for further analysis.

In some embodiments, temperature sensing can include a thermistor, Platinum Resistance Thermometer (PRT), other analog temperature sensor or, optionally, may be a temperature sensor with integrated digital circuitry that provides a digital output. Analogue temperature sensors can include a Temperature Conditioning Circuit (TCC), which incorporates electronic components that provide for proper voltage and output levels for the Analog to Digital (A/D) input to the microcontroller. If the temperature sensor is a digital output device, it can be connected directly to a Serial Programming Interface (SPI) bus or I2C bus associated with the microcontroller. In some embodiments, the temperature sensor may be calibrated or, optionally, may have inherent temperature measuring accuracy that facilitates an acceptable temperature accuracy, such as to a +/−0.1 degree Celsius accuracy, for example. Characteristics of the temperature sensor output function may be programmed into the memory to improve accuracy.

Chemical parameters may also be sensed and/or measured by one or more biosensors contained in the vaginal ring sensor device 10, 100, or 200. Biosensors may include electrochemical sensors and/or photometric sensors. In an exemplary embodiment, the biosensor may relate to a photometric sensing of glucose concentration based on a fluorescence sensor typology. In another example, the biosensor may detect the presence of reaction products from a glucose oxidase interaction with portions of the analyte biosensor and the fluid sample.

Concentration changes of analyte biomarkers can be monitored using the one or more biosensors. The monitoring of the biomarkers may occur at a predetermined frequency or upon demand through a user interface and/or an activation sensor in the device. Biomarkers can include those correlated to glucose levels, depression, cardiac function, acute and chronic diseases, and such.

Vaginal ring sensor device 10, 100, or 200 and the user interface can alert the user, and/or a practitioner, of the sensed and/or measured physical and/or chemical property. The alert can be programmed to occur when the levels measured are outside the predetermined threshold values programmed, received and/or calculated by the device. In addition in some embodiments, the data and alerts may be analyzed to perform one or more steps of: a) change measurement frequency according to the time of the day, b) identify personal patters in the changes of concentration levels measures, and c) change the measurement frequency according to the changes in property measured.

In some embodiments, the time of the day may change the frequency of measurements. For example, since device remains in the vaginal vault during sleep, the number of measurements during 10 PM and 6 AM can decrease or stop. Similarly, during lunch and dinner times the frequency may increase to detect changes due to the food consumption of the user. Changes in physical and/or chemical property may be identified by the system. Using the identified patterns, the system may alert the user of causes and/or, change the frequency according to the identified changes so that the system is more alert during critical identified conditions. Critical conditions can include events that would trigger significant changes in one or more physical and/or chemical property. Events can include, for example, holiday dates, exercise, location, time of the day, consumption of medicaments and the like.

In some embodiments, the originally programmed values may be customized, periodically or in real time, according to identified patterns/conditions. This ability may allow the system to increase its effectiveness by eliminating false alarms and increasing sensitivity at a critical condition. Effectiveness can promote user participation with the system thereby maximizing the benefits of the device and thereby providing a safe monitoring system. Data relating to the user including, for example, the identified patterns, measurements, and/or preferences may become part of the medical history of the user. Medical history may be stored securely by encrypting the data and/or restricting its access.

In some embodiments, vaginal ring sensor device 10, 100, or 200 of the invention may also have at least one depression or blind hole located on the surface of the device. The depression or blind hole may contain a therapeutic, or active, agents for delivery to the vaginal vault, allowing the vaginal ring sensor device to act as a drug delivery device.

Therapeutic agents that may be used in conjunction with the vaginal ring sensor device 10, 100, or 200 described herein include, but are not limited to: small molecules; proteins; peptides; nucleotides; nucleic acids; carbohydrates; simple sugars; cells; genes; anti-thrombotics; anti-metabolics; anticoagulants; antimitotics; fibrinolytics; anti-inflammatory steroids; monoclonal antibodies; vitamins; sedatives; steroids; hypnotics; antiinfectives, such as antibiotics and antiviral agents; chemotherapeutic agents (i.e., anticancer agents); prostaglandins, radiopharmaceuticals, anti-rejection agents; analgesics; anti-inflammatory agents; hormones, such as steroids; growth factors (inhibitors and promoters), such as epidermal growth factor, fibroblast growth factor, platelet-derived growth factor, insulin-like growth factor, transforming growth factors, and vascular endothelial growth factor; anti-angiogenic proteins such as endostatin; polysaccharides; glycoproteins; lipoproteins; and any combination of these.

Figure 7:
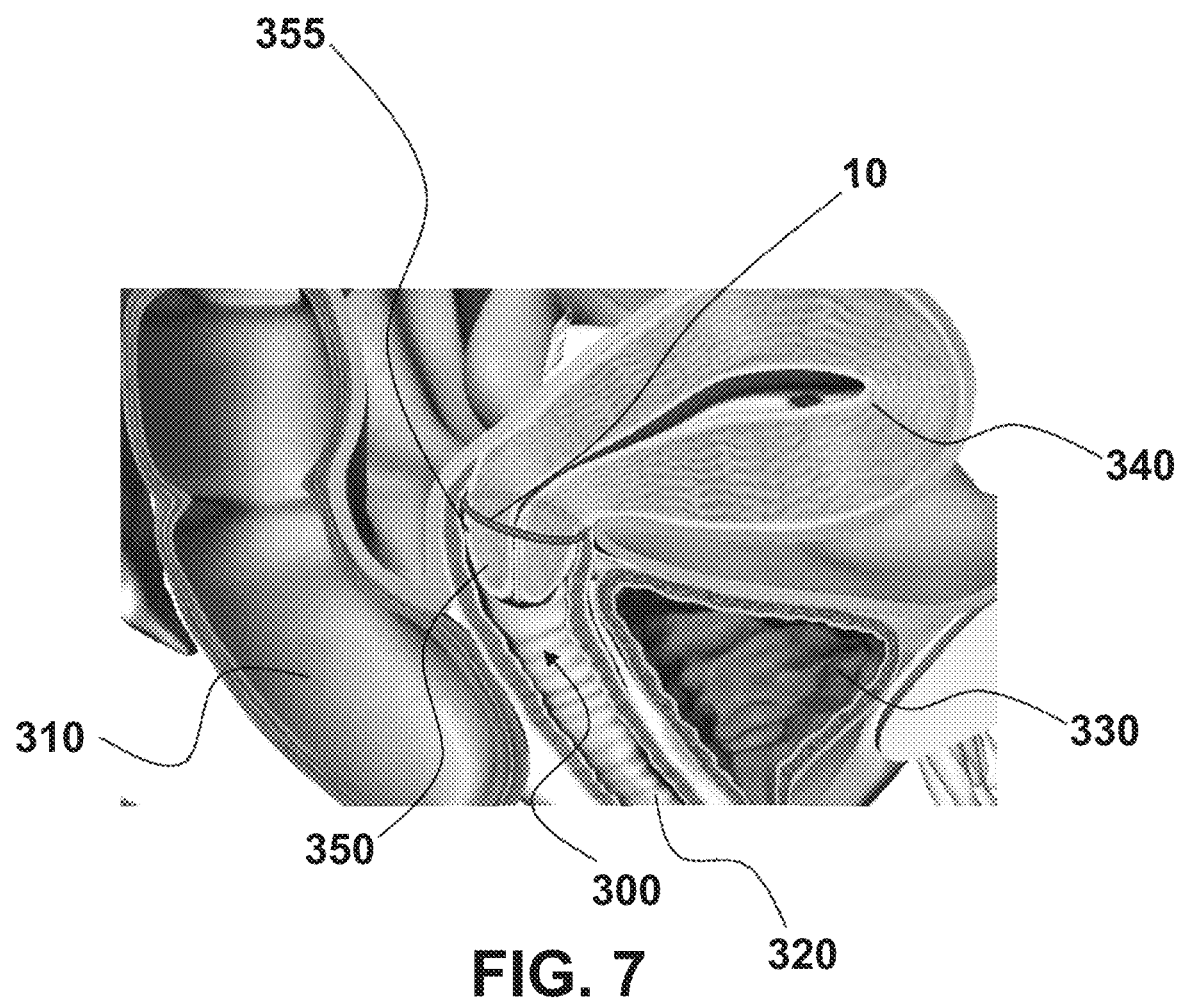
FIG. 7 is an illustration depicting a vaginal ring sensor device according to the present invention arranged within the vaginal vault of a human female.

FIG. 7 is a schematic diagram depicting the location an embodiment of a vaginal ring sensor device 10 of the invention when placed in the vaginal vault 300 of a human female. The figure shows the anatomy of the pelvic region of a human female, including the rectum 310, vagina 320, the bladder 330, the uterus 340, the cervix 350, and ecto-cervix 355. Vaginal ring sensor device 10 is disposed on the ectocervix 355, where it remains for the period of time for which it is in use. The vaginal ring sensor device 10 is structured and arranged to adapt to the natural expansion and contraction of the cervix over the course of a woman's monthly menstrual cycle, and thus can be comfortably worn throughout the menstrual cycle.

Vaginal ring sensor devices 10, 100, 200 according to the present invention may be placed in the vaginal vault of a human female by the user herself, or may be placed by a medical professional such as a doctor, doctor's aide, nurse, or nurse practitioner. The vaginal ring sensor device 10 is designed to remain in place in the vaginal vault of a human female for an extended period of time, allowing for the monitoring of physiological parameters in the vaginal vault of a female user for an extended period of time. An extended period of time can be greater than two days, or one week, or one month, or three months, or six months, one year or greater. Once inserted the vaginal ring sensor 10, 100, 200 according to the present can sense and/or measure one or more parameters of the vaginal fluid. The one or more sensed and/or measured parameters can be stored by the device and/or transmitted as described above.

Accordingly, embodiments of the present invention may include a method to use a vaginal ring sensor device including: inserting a vaginal ring sensor device having at least one through hole the passes through a ring body of the vaginal ring sensor device into the vaginal vault of a user; and measuring and/or sensing at least one parameter of a vaginal fluid that passes through the at least one through hole. The measured parameter may be any one of a number of different physiological parameters including physical and chemical parameters. Of course a single parameter may be sensed and/or measured or multiple parameters may be sensed and/or measured. The method may further include storing and/or transmitting the sensed and/or measured parameter information.

Specific examples and method steps have been described herein to explain and enable different aspects of the present invention. These method steps and examples are for illustration purposes and are not intended to limit the scope of the claims in any manner. Accordingly, the description is intended to embrace all embodiments that may be apparent to those skilled in the art.

We claim:

1. A vaginal ring sensor device comprising:
   a ring body having a center through hole configured to be inserted and securely retained within the vaginal vault of a user during use;
   at least one other through hole which passes through the ring body;
   at least one biosensor structured and arranged to sense and/or measure a parameter of vaginal fluid as such fluid passes through said at least one other through hole.

2. The vaginal ring sensor device according to claim 1, wherein the ring body has the shape of a circle, rectangle, rounded rectangle, oval, square, triangle, race track, or square.

3. The vaginal ring sensor device according to claim 1, wherein the ring body has a circular, rectangular, rounded rectangular, oval, square, triangular, race track, square, or x-shaped cross-section.

4. The vaginal ring sensor device according to claim 1, wherein the at least one other through hole is structured and arranged to permit the flow of fluids through the ring body immediately upon insertion of the device into the vaginal vault of a female user.

5. The vaginal ring sensor device according to claim 3, wherein the cross-section of the ring body measures from about 7 mm to about 10 mm.

6. The vaginal ring sensor device according to claim 1, wherein the at least one other through hole includes a first opening and a second opening, the at least one other through hole defining a through surface extending through the ring body from the first opening to the second opening.

7. The vaginal ring sensor device according to claim 1, wherein the ring body has a radius of from about 2 cm to about 3 cm as measured from a center of a hole defined by the ring body to an outer surface of the ring body.

8. The vaginal ring sensor device according to claim 1, wherein the at least one biosensor is partially embedded into a wall of a through surface of the ring body.

9. The vaginal ring sensor device according to claim 1, wherein the at least one biosensor is secured to a wall of a through surface of the ring body.

10. The vaginal ring sensor device according to claim 1, further comprising at least one biosensor arranged on an outer surface of the ring body.

11. The vaginal ring sensor device according to claim 1, further comprising at least one biosensor arranged on an inner surface of the ring body.

12. A vaginal ring sensor device comprising:
    a ring body configured to be inserted and securely retained within the vaginal vault of a user during use;
    a plurality of through holes that pass through the ring body;
    at least one biosensor structured and arranged to sense and/or measure a parameter of vaginal fluid as such fluid passes through at least one of the through holes.

13. The vaginal ring sensor device according to claim 12, wherein the ring body has the shape of a circle, rectangle, rounded rectangle, oval, square, triangle, race track, or square.

14. The vaginal ring sensor device according to claim 12, wherein the ring body has a circular, rectangular, rounded rectangular, oval, square, triangular, race track, square, or x-shaped cross-section.

15. The vaginal ring sensor device according to claim 12, wherein each of the plurality of through holes is structured and arranged to permit the flow of fluids through the ring body immediately upon insertion of the device into the vaginal vault of a female user.

16. The vaginal ring sensor device according to claim 14, wherein the cross-section of the ring body measures from about 7 mm to about 10 mm.

17. The vaginal ring sensor device according to claim 12, wherein each through hole includes a first opening and a second opening, the through hole defining a through surface extending through the ring body from the first opening to the second opening.

18. The vaginal ring sensor device according to claim 12, wherein the ring body has a radius of from about 2 cm to about 3 cm as measured from a center of a hole defined by the ring body to an outer surface of the ring body.

19. The vaginal ring sensor device according to claim 12, wherein the at least one biosensor is partially embedded into a wall of a through surface of the ring body.

20. The vaginal ring sensor device according to claim 12, wherein the at least one biosensor is secured to a wall of a through surface of the ring body.

21. The vaginal ring sensor device according to claim 12, further comprising at least one biosensor arranged on an outer surface of the ring body.

22. The vaginal ring sensor device according to claim 12, further comprising at least one biosensor arranged on an inner surface of the ring body.

23. The vaginal ring sensor device according to claim 12, wherein the at least one biosensor comprises a plurality of biosensors, and wherein each one of said biosensors is structured and arranged to sense and/or measure a parameter of vaginal fluid as such fluid passes through one of said plurality of through holes.

24. The vaginal ring sensor device according to claim 12, wherein the at least one biosensor comprises a first pair of biosensors.

25. The vaginal ring sensor device according to claim 24, wherein each one of the first pair of biosensors is located within a respective one of a first pair of through holes.

26. The vaginal ring sensor device according to claim 25, wherein each one of the first pair of through holes is directionally aligned with the other one of the first pair respective through holes on opposite sides of the ring body.

27. The vaginal ring sensor device according to claim 26, further comprising a second pair of biosensors.

28. The vaginal ring sensor device according to claim 27, wherein each one of the second pair of biosensors is located within a respective one of a second pair of through holes.

29. The vaginal ring sensor device according to claim 28, wherein each one of the second pair of through holes is directionally aligned with the other one of the second pair respective through holes on opposite sides of the ring body.

* * * * *